US012797013B2

(12) United States Patent
Chiu et al.

(10) Patent No.: US 12,797,013 B2
(45) Date of Patent: Nov. 17, 2026

(54) SYSTEM AND METHOD FOR OPTICAL SENSOR MEASUREMENT CONTROL

(71) Applicant: Artilux, Inc., Menlo Park, CA (US)

(72) Inventors: Kai-Wei Chiu, Hsinchu County (TW); Chun-Wei Chang, Hsinchu County (TW); Jui-Wei Tsai, Hsinchu County (TW); Shih-Jie Wu, Hsinchu County (TW)

(73) Assignee: Artilux, Inc., Menlo Park, CA (US)

( * ) Notice: Subject to any disclaimer, the term of this patent is extended or adjusted under 35 U.S.C. 154(b) by 173 days.

(21) Appl. No.: 18/468,311

(22) Filed: Sep. 15, 2023

(65) Prior Publication Data

US 2024/0156410 A1 May 16, 2024

Related U.S. Application Data

(60) Provisional application No. 63/514,363, filed on Jul. 19, 2023, provisional application No. 63/384,949, (Continued)

(51) Int. Cl.
*A61B 5/00* (2006.01)
*A61B 5/024* (2006.01)

(52) U.S. Cl.
CPC ........ *A61B 5/7221* (2013.01); *A61B 5/02433* (2013.01); *A61B 5/6801* (2013.01); *A61B 5/6844* (2013.01); *A61B 2560/0209* (2013.01)

(58) Field of Classification Search
CPC . A61B 5/7221; A61B 5/02433; A61B 5/6801; A61B 5/6844; A61B 2560/0209;
(Continued)

(56) References Cited

U.S. PATENT DOCUMENTS 7,446,316 B2 11/2008 Kilgore et al.
9,687,671 B2 6/2017 Weckwerth et al.
(Continued)

FOREIGN PATENT DOCUMENTS

CN 107820410 12/2019
WO WO-2023180205 A1 * 9/2023 ........... H04R 1/1016

OTHER PUBLICATIONS

Roddiger T, Clarke C, Breitling P, Schneegans T, Zhao H, Gellersen H, Beigl M. Sensing with earables: A systematic literature review and taxonomy of phenomena. Proceedings of the ACM on interactive, mobile, wearable and ubiquitous technologies. Sep. 7, 2022;6(3):1-57 (Year: 2022).*

*Primary Examiner* — Anne M Kozak
*Assistant Examiner* — Jason P Gross
(74) *Attorney, Agent, or Firm* — Dority & Manning, P.A.

(57) ABSTRACT

Methods for determining a signal quality index for bioinformation measurement are disclosed herein. The method can include detecting a light intensity when the transmitter module is in an off state. The method can include comparing the light intensity to a first threshold. The method can include decreasing the gain of the receiver module when the light intensity is greater than the first threshold. The method can include comparing the light intensity to a second threshold when the light intensity is less than the first threshold. The method can include decreasing the gain of the receiver module when the light intensity is greater than the second threshold. The method can include comparing the light intensity to a third threshold when the light intensity is less than the second threshold. The method can include increasing the gain of the receiver module when the light intensity is less than the third threshold.

13 Claims, 14 Drawing Sheets

Related U.S. Application Data filed on Nov. 24, 2022, provisional application No. 63/383,076, filed on Nov. 10, 2022.

(58) Field of Classification Search
CPC ..... A61B 5/02416; A61B 5/681; A61B 5/024; A61B 5/025; A61B 5/026; A61B 5/0261; A61B 5/6802; A61B 5/6813; A61B 5/04; A61B 5/05; A61B 5/06; A61B 5/07; A61B 5/08; A61B 5/09
See application file for complete search history.

(56) References Cited

U.S. PATENT DOCUMENTS 12,089,931 B1 * 9/2024 Duan .................... A61B 5/6844
2005/0177929 A1 * 8/2005 Greenwald .............. A61B 5/11
73/865.9
2012/0018637 A1 1/2012 Mitani
2015/0201853 A1 * 7/2015 Hong .................. A61B 5/02427
600/479
2017/0090599 A1 * 3/2017 Kuboyama ........... G06F 3/0433
2017/0215747 A1 * 8/2017 van Dinther ......... A61B 5/6826
2017/0359635 A1 12/2017 Aumer et al.
2018/0289328 A1 * 10/2018 Hasegawa .......... A61B 5/14553
2019/0342651 A1 * 11/2019 Howell ................ H04R 1/1041
2020/0138377 A1 * 5/2020 Huijbregts ............. A61B 5/681
2022/0225006 A1 7/2022 Allec et al.
2022/0240858 A1 * 8/2022 Kleiser .............. A61B 5/14552
2022/0273207 A1 * 9/2022 Mohammadi ........ A61B 5/7221
2022/0276405 A1 * 9/2022 Watanabe ............. H10F 55/255
2022/0283623 A1 * 9/2022 Zhao ....................... G06F 3/014
2023/0247341 A1 * 8/2023 Saulsbury ............ A61B 5/6803
381/380
2023/0389812 A1 * 12/2023 Chung ............... A61B 5/02416
2024/0090784 A1 * 3/2024 Liu ........................ G04G 17/04
2025/0288252 A1 * 9/2025 Kirszenblat .......... A61B 5/6843

* cited by examiner

410

420

SYSTEM AND METHOD FOR OPTICAL SENSOR MEASUREMENT CONTROL

CROSS-REFERENCE TO RELATED APPLICATIONS

This patent application claims priority to U.S. Provisional Patent Application No. 63/383,076, filed Nov. 10, 2022, U.S. Provisional Patent Application No. 63/384,949, filed Nov. 24, 2022, and U.S. Provisional Patent Application No. 63/514,363, filed Jul. 19, 2023, the contents of which are hereby incorporated herein by reference in their entirety.

FIELD

The present application is related to a bioinformation measurement apparatus.

BACKGROUND

Optical sensors are being used in many systems, such as smartphones, wearable electronics, robotics, and autonomous vehicles, etc. for proximity detection, 2D/3D imaging, object recognition, image enhancement, material recognition, color fusion, health monitoring, and other relevant applications.

SUMMARY OF THE INVENTION

The present disclosure discloses a plurality of wearable devices each having an optical sensing apparatus, where each wearable device can determine signal quality index for bioinformation measurement and choose which bioinformation measurement to be transmitted, thereby improving metric quality and saving power consumption. The optical sensing apparatus can be operable for different wavelength ranges, including visible (e.g., wavelength range 380 nm to 780 nm, or a similar wavelength range as defined by a particular application) and non-visible light. The non-visible light includes near-infrared (NIR, e.g., wavelength range from 780 nm to 1000 nm, or a similar wavelength range as defined by a particular application) and short-wavelength infrared (SWIR, e.g., wavelength range from 1000 nm to 3000 nm, or a similar wavelength range as defined by a particular application) light.

One aspect of the present disclosure is directed to a method for a device which includes a transmitter module and a receiver module to adjust a gain of the receiver module. The method includes detecting, by the receiver module, a received light intensity when the transmitter module is in OFF_STATE. The method includes comparing, by the device, the received light intensity to a first threshold. The method includes decreasing, by the device, the gain of the receiver module when the received light intensity is greater than the first threshold. The method includes comparing, by the device, the received light intensity to a second threshold when the received light intensity is less than the first threshold. The method includes decreasing, by the device, the gain of the receiver module when the received light intensity is greater than the second threshold. The method includes comparing, by the device, the received light intensity to a third threshold when the received light intensity is less than the second threshold. The method includes increasing, by the device, the gain of the receiver module when the received light intensity is less than the third threshold.

In some implementations, the method includes discarding a detection result of the receiver module when the received light intensity is greater than the first threshold.

In some implementations, the method includes performing a detection determination process when the received light intensity is less than the first threshold and greater than the second threshold.

In some implementations, the method includes, performing a detection determination process when the received light intensity is less than the third threshold.

In some implementations, the detection determination process can include proximity detection, skin detection, or bioinformation measurement.

In some implementations, the first threshold is greater than the second threshold, and the second threshold is greater than the third threshold.

In some implementations, the receiver module includes an ADC, the received light intensity can be obtained from an output of the ADC.

Another aspect of the present disclosure is directed to a method for a device comprising a skin detection circuitry to wake up from a power-saving mode. The method includes performing, by the skin detection circuitry, a skin detection function when the device operates in the power-saving mode. The method includes determining, by the skin detection circuitry, a detection result indicating a presence of skin. The method includes, in response to determining the detection result indicating the presence of skin, outputting, by the skin detection circuitry, a signal that causes the device to exit the power-saving mode and to operate in a normal mode.

In some implementations, the device includes a SOC, the SOC operates at low power when the device operates in the power-saving mode.

In some implementations, the device includes a sensor configured to provide sensor data to the skin detection circuitry to determine the detection result.

Another aspect of the present disclosure is directed to a method for operating a wearable device to detect a presence of skin. The method includes receiving, by a receiver module of the wearable device at a first time, a first light with a first wavelength and a second light with a second wavelength. The method includes calculating, by a circuitry of the wearable device, a first ratio between an intensity of the first light and an intensity of the second light. The method includes determining, by the circuitry of the wearable device, the presence of the skin based on a comparison between the first ratio and a first threshold associated with skin detection. The method includes receiving, by the receiver module of the wearable device at a second time, a third light with the first wavelength and a fourth light with the second wavelength. The method calculating, by the circuitry of the wearable device, a second ratio between an intensity of the third light and an intensity of the fourth light. The method includes determining, by the circuitry of the wearable device, an absence of the skin based on a comparison between the second ratio and a second threshold associated with skin detection, wherein the first threshold associated with skin detection is different from the second threshold associated with skin detection.

In some implementations, the method includes receiving, by the receiver module of the wearable device at a third time that is prior to the first time, a fifth light with the first wavelength. In some implementations, the method includes determining, by the circuitry of the wearable device, that the wearable device is proximity to an object based on a comparison between an intensity of the fifth light and a first threshold associated with proximity detection. In some implementations, the method includes receiving, by the receiver module of the wearable device at a fourth time that is later than the third time, a sixth light with the first wavelength. In some implementations, the method includes determining, by the circuitry of the wearable device, that the wearable device is far from the object based on a comparison between an intensity of the sixth light and a second threshold associated with proximity detection, wherein the first threshold associated with proximity detection is different from the second threshold associated with proximity detection.

In some implementations, the first threshold associated with the skin detection is higher than the second threshold associated with skin detection.

In some implementations, the method includes calculating, by the circuitry of the wearable device, a signal quality associated with a sensor measurement information, and determining to perform a bioinformation measurement based on a comparison between the signal quality associated with the sensor measurement information and a first threshold associated with signal quality.

In some implementations, the method includes determining to stop the bioinformation measurement based on a comparison between the signal quality associated with the sensor measurement information and a second threshold associated with signal quality.

In some implementations, the signal quality associated with the sensor measurement information includes a weighted calculation of one or more of an AC signal amplitude of a particular sensor measurement, a signal-to-noise ratio of the particular sensor measurement, a DC drift variation of the particular sensor measurement, a stability of the particular sensor measurement, or a validity of the particular sensor measurement.

In some implementations, the bioinformation includes a heart rate of a user.

In some implementations, calculating, by the circuitry of the wearable device, the signal quality includes calculating the signal quality after determining that the skin is present.

In some implementations, the first wavelength is within an NIR wavelength range and the second wavelength is within a SWIR wavelength range.

In some implementations, the first wavelength and the second wavelength are within a SWIR wavelength range.

Another aspect of the present disclosure is directed to a method for a device which includes a transmitter module and a receiver module to adjust a gain of the receiver module. The method includes detecting, by the receiver module, a received light intensity when the transmitter module is in OFF_STATE. The method includes, comparing, by the device, the received light intensity to a first threshold. The method includes decreasing, by the device, the gain of the receiver module when the received light intensity is greater than the first threshold. The method includes comparing, by the device, the received light intensity to a second threshold when the received light intensity is less than the first threshold. The method includes decreasing, by the device, the gain of the receiver module when the received light intensity is greater than the second threshold. The method includes comparing, by the device, the received light intensity to a third threshold when the received light intensity is less than the second threshold. The method includes increasing, by the device, the gain of the receiver module when the received light intensity is less than the third threshold.

In some implementations, the method includes discarding a detection result of the receiver module when the received light intensity is greater than the first threshold.

In some implementations, the method includes performing a detection determination process when the received light intensity is less than the first threshold and greater than the second threshold.

In some implementations, the method includes performing a detection determination process when the received light intensity is less than the third threshold.

In some implementations, the detection determination process can include proximity detection, skin detection, or bioinformation measurement.

In some implementations, the first threshold is greater than the second threshold, and the second threshold is greater than the third threshold.

In some implementations, the receiver module includes an ADC, the received light intensity can be obtained from an output of the ADC.

Another aspect of the present disclosure is directed to a method for a device including a skin detection circuitry to wake up from a power-saving mode. The method includes performing, by the skin detection circuitry, a skin detection function when the device operates in the power-saving mode. The method includes determining, by the skin detection circuitry, a detection result indicating a presence of skin. The method includes in response to determining the detection result indicating the presence of skin, outputting, by the skin detection circuitry, a signal that causes the device to exit the power-saving mode and to operate in a normal mode.

In some implementations, the device includes a SOC, the SOC operates at low power when the device operates in the power-saving mode.

In some implementations, the device includes a sensor configured to provide sensor data to the skin detection circuitry to determine the detection result.

Another aspect of the present disclosure is directed to a method for transmitting sensor measurement information. The method includes obtaining, by a first sensor of a first device, first sensor measurement information representing a particular type of bioinformation measured from a first part of a user. The method includes obtaining, by a second sensor of a second device, second sensor measurement information representing the particular type of bioinformation measured from a second part of the user. The method includes determining, by the first device, one or more first characteristics associated with the first sensor measurement information. The method includes determining, by the second device, one or more second characteristics associated with the second sensor measurement information. The method includes determining, by one or more of the first device, the second device, or a third device, that the first device is to transmit sensor measurement information to the third device based on a comparison between the one or more first characteristics and the one or more second characteristics. The method includes in response to determining that the first device is to send the sensor measurement information to the third device, controlling the second sensor to enter into a power-saving mode.

In some implementations, controlling the second sensor to enter into the power-saving mode includes controlling, by one or more of the first device, the second device, or the third device, the second sensor to stop obtaining the second sensor measurement information.

In some implementations, determining that the first device is to transmit the sensor measurement information to the third device includes transmitting, from the first device to the third device, the first sensor measurement information. In some implementations, determining that the first device is to transmit the sensor measurement information to the third device includes transmitting, from the second device to the third device, the second sensor measurement information. In some implementations, determining that the first device is to transmit the sensor measurement information to the third device includes determining, by the third device, that the first device is to transmit the sensor measurement information to the third device based on the comparison between the first sensor measurement information and the second sensor measurement information.

In some implementations, controlling the second sensor to stop obtaining the second sensor measurement information further includes transmitting, by the third device, control data to the second device to cause the second sensor to stop obtaining the second sensor measurement information.

In some implementations, determining that the first device is to transmit the sensor measurement information to the third device includes transmitting, from the first device to the second device, first characteristics data representing the one or more first characteristics associated with the first sensor measurement information. In some implementations, determining that the first device is to transmit the sensor measurement information to the third device includes transmitting, from the second device to the first device, second characteristics data representing the one or more second characteristics associated with the second sensor measurement information. In some implementations, determining that the first device is to transmit the sensor measurement information to the third device includes determining, by each of the first device and the second device, that the first device is to transmit the sensor measurement information to the third device based on the comparison between the one or more first characteristics and the one or more second characteristics.

In some implementations, controlling the second sensor to stop obtaining the second sensor measurement information includes transmitting, by the second device, a control signal to the second sensor to stop obtaining the second sensor measurement information.

In some implementations, controlling the second sensor to stop obtaining the second sensor measurement information includes transmitting, by the first device, control data to the second device to cause the second sensor to stop obtaining the second sensor measurement information.

In some implementations, controlling the second sensor to enter into a power-saving mode includes controlling, by one or more of the first device, the second device, or the third device, the second sensor to stop transmitting the second sensor measurement information.

In some implementations, the first device and the second device include wireless earphones, and wherein the first part and the second part of the user include portions of the user's skin in contact with the wireless earphones.

In some implementations, the one or more first characteristics include one or more of a battery power of the first device or a signal quality associated with the first sensor measurement information.

In some implementations, the signal quality associated with the first sensor measurement information includes a weighted calculation of one or more of an AC signal amplitude of a particular sensor measurement, a signal-to-noise ratio of the particular sensor measurement, a DC drift variation of the particular sensor measurement, a stability of the particular sensor measurement, or a validity of the particular sensor measurement.

In some implementations, the first senor and the second sensor comprise germanium-on-silicon photodetectors.

In some implementations, the first senor and the second sensor include III-V photodetectors.

In some implementations, the third device comprises a mobile computing device.

In some implementations, the particular type of bioinformation includes a heart rate of the user.

Another aspect of the present disclosure is directed to a system. The system includes a first wearable device including a first sensor, the first wearable device configured to obtain first sensor measurement information representing a particular type of bioinformation measured from a first part of a user. The first wearable device is configured to determine one or more first characteristics associated with the first sensor measurement information. The system includes a second wearable device including a second sensor, the second wearable device configured to obtain second sensor measurement information representing the particular type of bioinformation measured from a second part of the user. The second wearable device is configured to determine one or more second characteristics associated with the second sensor measurement information. The system includes a computing device configured to determine that the first device is to transmit sensor measurement information to the third device based on a comparison between the one or more first characteristics and the one or more second characteristics. The computing device is configured to, in response to determining that the first device is to send the sensor measurement information to the third device, control the second sensor to enter into a power-saving mode.

In some implementations, controlling the second sensor to enter into the power-saving mode includes sending a signal to the second wearable device to cause the second sensor to stop obtaining the second sensor measurement information.

In some implementations, controlling the second sensor to enter into the power-saving mode includes sending a signal to the second wearable device to cause the second wearable device to stop transmitting the second sensor measurement information.

Another aspect of the present disclosure is directed to a system. The system includes a first wearable device comprising a first sensor, the first wearable device configured to obtain first sensor measurement information representing a particular type of bioinformation measured from a first part of a user. The first wearable device is configured to determine one or more first characteristics associated with the first sensor measurement information. The system includes a second wearable device including a second sensor, the second wearable device configured to obtain second sensor measurement information representing the particular type of bioinformation measured from a second part of the user. The second wearable device is configured to determine one or more second characteristics associated with the second sensor measurement information. The second wearable device is configured to obtain the one or more first characteristics from the first wearable device. The second wearable device is configured to determine that the first device is to transmit sensor measurement information to the third device based on a comparison between the one or more first characteristics and the one or more second characteristics. The second wearable device is configured, to in response to determining that the first device is to send the sensor measurement information to the third device, control the second sensor to enter into a power-saving mode.

In some implementations, controlling the second sensor to enter into the power-saving mode includes controlling the second sensor to stop obtaining the second sensor measurement information.

Another aspect of the present disclosure is directed to a method for operating a wearable device to detect a presence of skin. The method includes receiving, by a receiver module of the wearable device at a first time, a first light with a first wavelength and a second light with a second wavelength. The method includes calculating, by a circuitry of the wearable device, a first ratio between an intensity of the first light and an intensity of the second light. The method includes determining, by the circuitry of the wearable device, the presence of the skin based on a comparison between the first ratio and a first threshold associated with skin detection. The method includes receiving, by the receiver module of the wearable device at a second time, a third light with the first wavelength and a fourth light with the second wavelength. The method includes calculating, by the circuitry of the wearable device, a second ratio between an intensity of the third light and an intensity of the fourth light. The method includes determining, by the circuitry of the wearable device, an absence of the skin based on a comparison between the second ratio and a second threshold associated with skin detection, wherein the first threshold associated with skin detection is different from the second threshold associated with skin detection.

In some implementations, the method includes receiving, by the receiver module of the wearable device at a third time that is prior to the first time, a fifth light with the first wavelength. In some implementations, the method includes determining, by the circuitry of the wearable device, that the wearable device is proximity to an object based on a comparison between an intensity of the fifth light and a first threshold associated with proximity detection. In some implementations, the method includes receiving, by the receiver module of the wearable device at a fourth time that is later than the third time, a sixth light with the first wavelength. In some implementations, the method includes determining, by the circuitry of the wearable device, that the wearable device is far from the object based on a comparison between an intensity of the sixth light and a second threshold associated with proximity detection, wherein the first threshold associated with proximity detection is different from the second threshold associated with proximity detection.

In some implementations, the first threshold associated with the skin detection is higher than the second threshold associated with skin detection.

In some implementations, the method includes calculating, by the circuitry of the wearable device, a signal quality associated with a sensor measurement information, and determining to perform a bioinformation measurement based on a comparison between the signal quality associated with the sensor measurement information and a first threshold associated with signal quality.

In some implementations, the method includes determining to stop the bioinformation measurement based on a comparison between the signal quality associated with the sensor measurement information and a second threshold associated with signal quality.

In some implementations, the signal quality associated with the sensor measurement information includes a weighted calculation of one or more of an AC signal amplitude of a particular sensor measurement, a signal-to-noise ratio of the particular sensor measurement, a DC drift variation of the particular sensor measurement, a stability of the particular sensor measurement, or a validity of the particular sensor measurement.

In some implementations, the bioinformation includes a heart rate of a user.

In some implementations, calculating, by the circuitry of the wearable device, the signal quality includes calculating the signal quality after determining that the skin is present.

In some implementations, the first wavelength is within an NIR wavelength range and the second wavelength is within a SWIR wavelength range.

In some implementations, the first wavelength and the second wavelength are within a SWIR wavelength range.

In some implementations, the receiver module comprises germanium-on-silicon photodetectors.

In some implementations, the receiver module comprises III-V photodetectors.

Another aspect of the present disclosure is directed to a device. The device includes a sensor comprising a receiver module and a circuitry wherein the sensor is configured to receive, by the receiver module at a first time, a first light with a first wavelength and a second light with a second wavelength. The sensor is configured to calculate, by the circuitry, a first ratio between an intensity of the first light and an intensity of the second light. The sensor is configured to determine, by the circuitry, the presence of the skin based on a comparison between the first ratio and a first threshold associated with skin detection. The sensor is configured to receive, by the receiver module at a second time, a third light with the first wavelength and a fourth light with the second wavelength. The sensor is configured to calculate, by the circuitry, a second ratio between an intensity of the third light and an intensity of the fourth light. The sensor is configured to determine, by the circuitry, an absence of the skin based on a comparison between the second ratio and a second threshold associated with skin detection, wherein the first threshold associated with skin detection is different from the second threshold associated with skin detection.

BRIEF DESCRIPTION OF THE DRAWINGS

The foregoing aspects and many of the advantages of this application will become more readily appreciated as the same becomes better understood by reference to the following detailed description, when taken in conjunction with the accompanying drawings.

DETAILED DESCRIPTION

Figure 1:
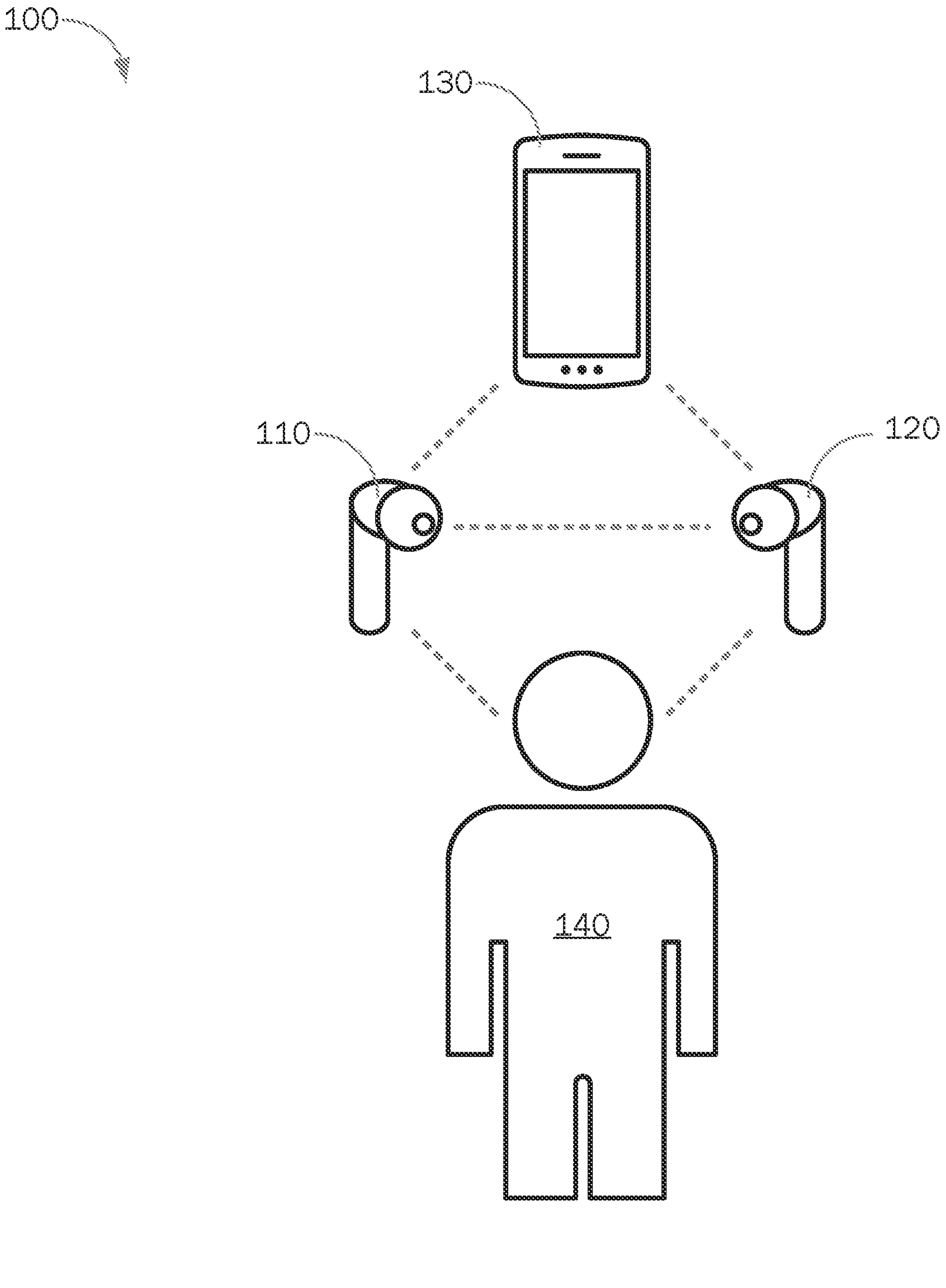
FIG. 1 shows an example of an optical sensing system.

The following embodiments accompany the drawings to illustrate the concept of the present disclosure. In the drawings or descriptions, similar or identical parts use the same reference numerals, and in the drawings, the shape, thickness or height of the element can be reasonably expanded or reduced. The embodiments listed in the present application are only used to illustrate the present application and are not used to limit the scope of the present application. Any obvious modification or change made to the present application does not depart from the spirit and scope of the present application.

In general, an optical sensor can be used to measure various bioinformation from a user. For example, a photoplethysmogram (PPG) is an optically obtained plethysmogram, which can be used to determine various bioinformation such as heart rate, calories, skin moisture, $SpO_2$, blood pressure, etc. In some cases, a user may be wearing multiple wearable devices each having one or more optical sensors that are capable of measuring bioinformation. For example, a user may be wearing a pair of earbuds, where each earbud includes an optical sensor that can measure bioinformation of the user. However, based on a variety of factors (e.g., cleanness of an earbud, the earbud location relative to the ear, the battery level of the earbud, sweat, etc.), the signal quality of the bioinformation measurement from each wearable device may be different. It would therefore be desirable for an optical sensing system to select an optimal measurement signal from multiple measurement devices to provide more accurate measurement results. In addition, for those measurement devices that are not selected, they may enter a power-saving mode in order to save the overall system power and enhance the user's experience (e.g., longer music-listening time).

FIG. 1 shows an example of an optical sensing system 100. The optical sensing system 100 includes a first wearable device 110 (e.g., a first earbud, or any suitable wearable device such as glasses, helmet, wristband, watch, etc.), a second wearable device 120 (e.g., a second earbud, or any suitable wearable device), and a computing device 130 (e.g., mobile phone) for a user 140. In general, the user 140 can use the wearable devices 110 and 120 to perform one or more types of bioinformation measurements (e.g., heart rate, calories, skin moisture, SpO2, blood pressure, etc.). In some implementations, the wearable devices 110 and 120 may not have a display, and therefore may transmit the measured bioinformation to the computing device 130 for display and/or further processing.

Figure 3:
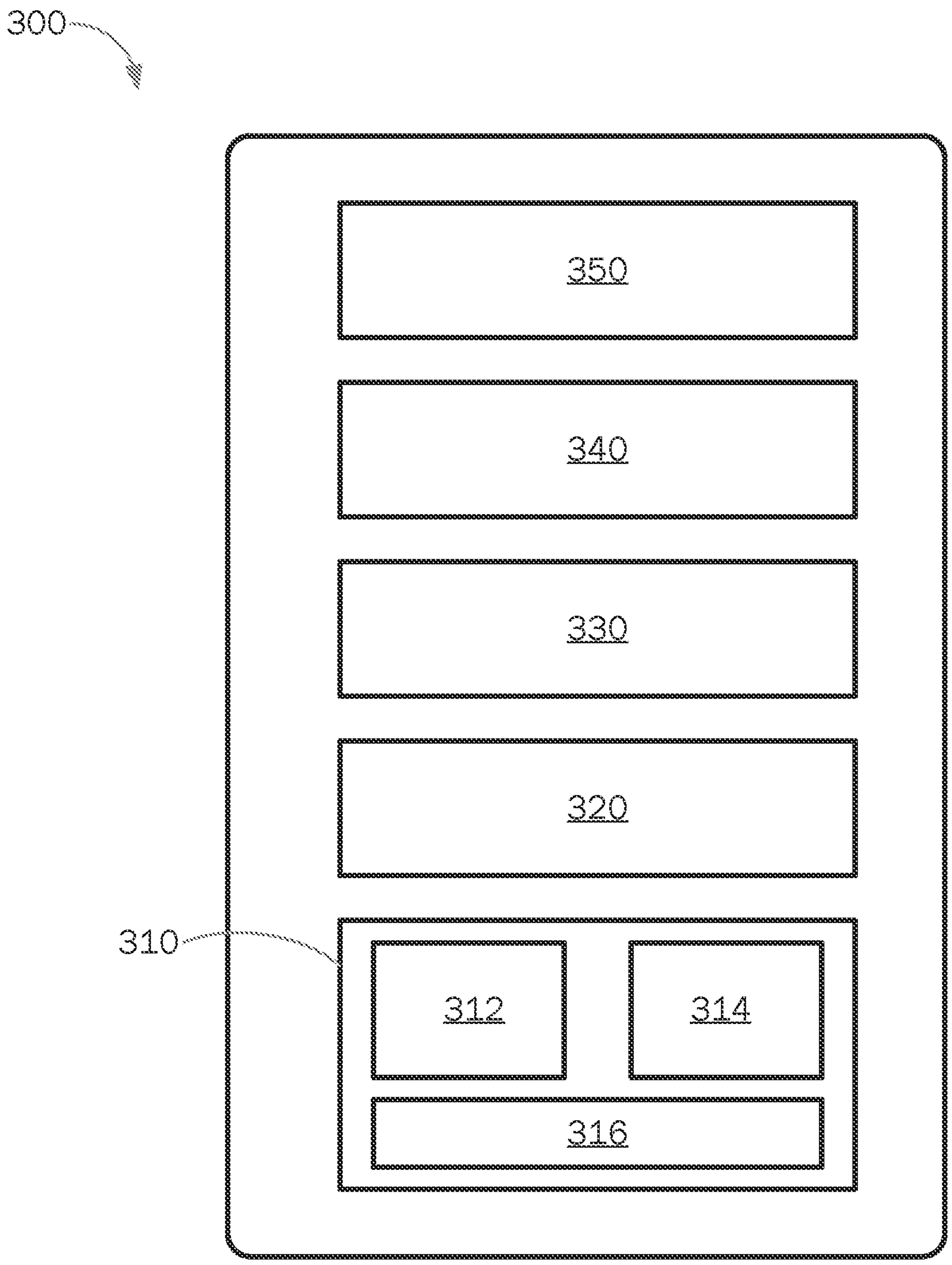
FIG. 3 shows an example of a wearable device.

Each of the first wearable device 110 and the second wearable device 120 includes one or more sensors configured to obtain sensor measurement information (e.g., analog or digital readout) representing a particular type of bioinformation (e.g., heart rate, calories, skin moisture, $SpO_2$, blood pressure, etc.) measured from a part (e.g., ear) of the user 140. FIG. 3 illustrates a device 300 (e.g., an earbud), which can be an example of the first wearable device 110 or the second wearable device 120. The device 300 includes a sensor 310, an input module 320, an output module 330, a communication module 340, and other circuitry 350.

The sensor 310 includes a transmitter module 312, a receiver module 314, and control circuitry 316. In some implementations, the transmitter module 312 may include multiple light sources (e.g., a first light source with NIR wavelength and a second light source with SWIR wavelength, or two light sources with SWIR wavelengths). Light transmitted by the transmitter module 312 may be absorbed and/or reflected by an object that is in proximity to the device 300.

The receiver module 314 is configured to detect the multi-band reflected lights which includes at least two lights at different wavelengths. The receiver module 314 can detect the visible light, or the non-visible light according to the application. The visible light can include blue, navy, green, yellow, or red light. The non-visible light can include NIR or SWIR. The receiver module 314 may include one or more photodetectors. In some embodiments, one or more photodetectors of the receiver module 314 may be a photodetector for three-dimensional (3D) depth sensing (e.g., i-TOF or d-TOF photodetector), proximity sensing, optical spectroscopy, two-dimensional (2D) sensing (e.g., 2D IR imaging), or a combination thereof. Each of the photodetectors can be implemented using a single photodiode or an array of photodetector pixels (e.g., 1D or 2D photodetector array as described in reference to FIGS. 7 and 8).

The control circuitry 316 can be configured to control the transmitter module 312 and the receiver module 314, and process the signal received by the receiver module 314 to obtain the bioinformation. The control circuitry 316 can be implemented by digital processor (DSP), general purpose processor, application-specific integrated circuit (ASIC), digital circuitry, software, or any combinations thereof.

The input module 320 is configured to receive one or more inputs (e.g., voice, haptic, etc.) from a user of the device 300. The output module 330 is configured to provide one or more outputs (e.g., display, voice, vibration, etc.) to the user of the device 300. The communication module 340 is configured to transmit and receive electrical signals from the device 300 to one or more other devices, and vice versa, via one or more communications protocols (e.g., WiFi, BLUEBOOTH, cellular, etc.). The other circuitry 350 can be any other circuitry (e.g., additional processing circuitry, memory, other sensors, etc.) equipped on the device 300.

Referring back to FIG. 1, the first wearable device 110 and the second wearable device 120 can each detect the presence of the skin and perform the bioinformation measurement, respectively. In some implementations, the first wearable device 110 and the second wearable device 120 can each determine one or more first characteristics associated with the first sensor measurement information and one or more second characteristics associated with the second sensor measurement information, respectively. In some implementations, the one or more first/second characteristics include a battery power level of the first wearable device 110 or the second wearable device 120. In some implementations, the one or more first/second characteristics include a signal quality associated with the respective sensor measurement information. The signal quality associated with a sensor measurement information may be one or more of an AC signal amplitude of a particular sensor measurement, a signal-to-noise ratio of the particular sensor measurement, a DC drift variation of the particular sensor measurement, a stability of the particular sensor measurement, a validity of the particular sensor measurement, or a weighted calculation of the above parameters. In some implementations, when the first wearable device 110 and/or the second wearable device 120 detects the presence of skin and the signal quality associated with a sensor measurement information is good enough to reach a threshold, the first wearable device 110 and/or the second wearable device 120 is allowed to perform the bioinformation measurement. In other words, the first wearable device 110 and/or the second wearable device 120 will perform the bioinformation measurement after confirming the presence of skin and the signal quality of the measurement information, for saving power consumption.

In some implementations, the signal quality associated with a sensor measurement information may be determined as a weighted sum of multiple parameters. For example, the signal quality associated with a sensor measurement information may be determined as:

$$\text{Signal Quality Index} = w_1 \times (AC_{signal_{amplitude}}) + w_2 \times (\text{Signal\_to\_noise\_ratio}) + w_3 \times (1 - DC\text{\_drift\_variation}),$$

where $w_1$, $w_2$, and $w_3$ are weighted values that sum to be 1.

As another example, the signal quality associated with a sensor measurement information may be determined as:

$$\text{Signal Quality Index} = w_4 \times (\text{heart\_beat\_stability}) + w_5 \times (\text{heart\_beat\_valid}),$$

where $w_4$, and $w_5$ are weighted values that sum to be 1.

Figure 4A:
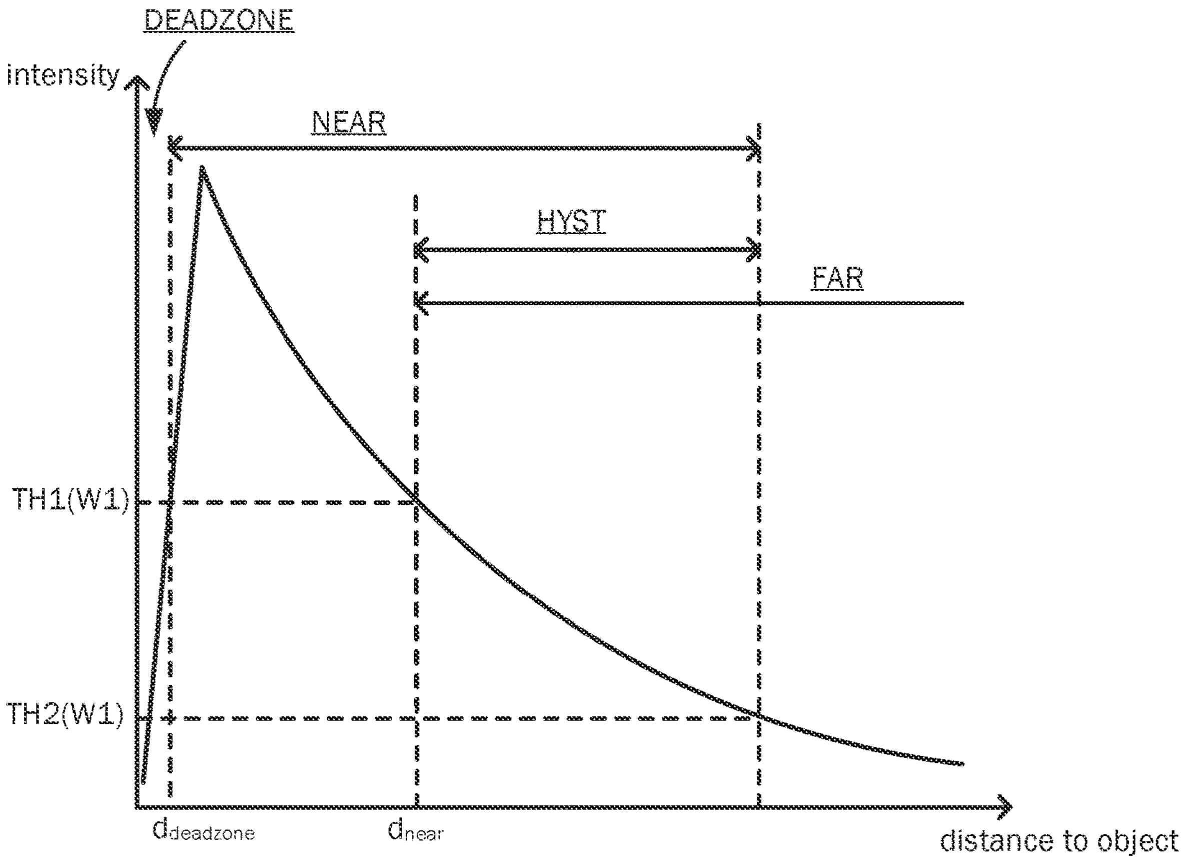
FIG. 4A shows an example of an intensity response of the sensor measurement from the sensor.

FIG. 4A shows an example of an intensity response of the sensor measurement from the sensor. The intensity response measured by the receiver module 314 decreases as the distance between the sensor 310 and the object increases. The object can be a human or other living creature. However, when the distance between the sensor 310 and the object is extremely close (e.g., less than 1 mm), the intensity will drop sharply because the reflected light cannot reach the receiver. In this situation, the intensity response may be lower than when the distance between the sensor 310 and the object is farther, so the wearable device may make incorrect distance determinations due to a sharp drop in intensity. In detail, referring to FIG. 4A, when the wearable device is far away from the object, the wearable device is regarded as in the FAR state, for example, the distance between the object and the sensor is greater than $d_{near}$. When the wearable device is close to the object, the wearable device is regarded as in the NEAR state, for example, the distance between the object and the sensor is less than $d_{near}$. When the wearable device is extremely close to the object, the wearable device is regarded as in the DEADZONE state, for example, the distance between the object and the sensor is less than $d_{deadzone}$. In the DEADZONE state, the intensity decreases sharply as the distance between the sensor 310 and the object decreases.

Figure 4B:
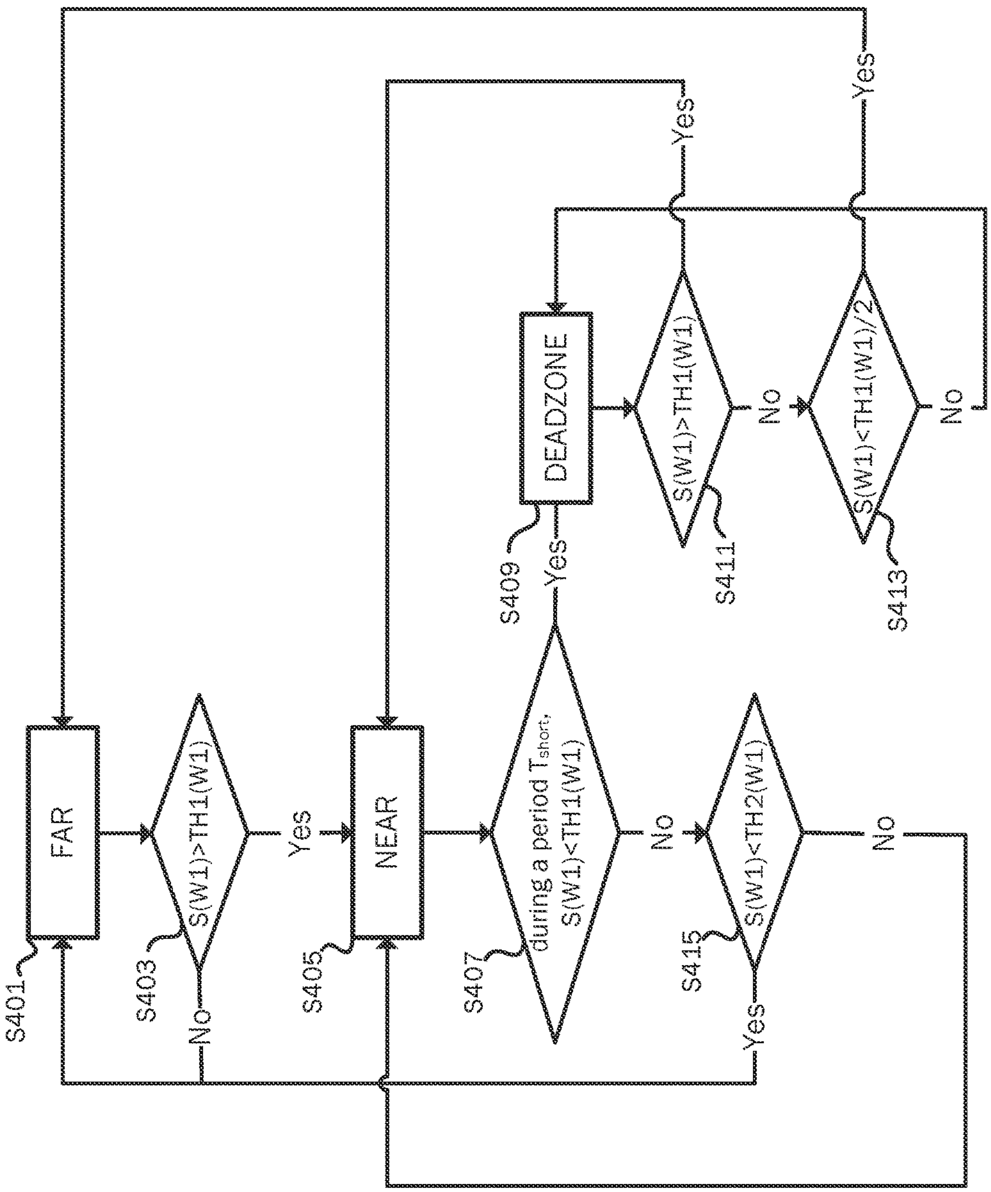
FIG. 4B shows an example of a flow of the wearable device for proximity detection.

FIG. 4B shows an example of a proximity detection flow 410 of the wearable device aforementioned for proximity detection. In an implementation, the proximity detection flow 410 can be implemented by the control circuitry 316 shown in FIG. 3. The receiver module 314 of the wearable device can receive a first light with a first wavelength W1 and a second light with a second wavelength W2. In an implementation, the first light is NIR, and the second light is SWIR. Referring to FIGS. 4A and 4B, as shown in S401, when the wearable device is far away from the object and operates in the FAR state, the wearable device is configured to compare the intensity of first light S(W1) received from the receiver module 314 to a first threshold TH1(W1) associated with proximity detection, as shown in S403. As shown in S405, if the intensity of first light S(W1) is larger than the first threshold TH1(W1) associated with proximity detection, the wearable device is regarded as proximity to the object and enters into the NEAR state. Otherwise, the wearable device is regarded as far away from the object and stays in the FAR state. As shown in S407, when the wearable device is in the NEAR state, the wearable device is configured to compare the intensity of first light S(W1) to the first threshold TH1(W1) during a short period $T_{short}$. As shown in S409, if the intensity of first light S(W1) changes to less than the first threshold TH1(W1) within the short period $T_{short}$, the wearable device is regarded as extremely close to the object and enters the DEADZONE state. As shown in S411, when the wearable device is in the DEADZONE state, the wearable device is continuously configured to compare the intensity of first light S(W1) to the first threshold TH1(W1). If the intensity of first light S(W1) is greater than the first threshold TH1(W1), the wearable device leaves the DEADZONE state and returns to the NEAR state. As shown in S413, when the wearable device is in the DEADZONE state and the intensity of first light S(W1) is less than TH1(W1)/2, the wearable device is regarded as far away from the object and returns to the FAR state. Otherwise, the wearable device stays in the DEADZONE state. In this way, the wearable device can avoid regarding extremely close distances as far distances. As shown in S415, when the wearable device is in the NEAR state, the intensity of first light S(W1) does not change to less than the first threshold TH1(W1) within the short period $T_{short}$, the wearable device is configured to compare the intensity of first light S(W1) received from the receiver module 314 to a second threshold TH2(W1) associated with proximity detection. If the intensity of first light S(W1) is less than the second threshold TH2(W1) associated with proximity detection, the wearable device is regarded as far away from the object and returns to the FAR state. Otherwise, the wearable device is regarded as proximity to the object and stays in the NEAR state. In an implementation, when the wearable device is in the NEAR state, the wearable device can perform subsequent skin detection flow. The second threshold TH2(W1) associated with proximity detection is smaller than the first threshold TH1(W1) associated with proximity detection. The gap between the second threshold TH2(W1) and the first threshold TH1(W1) is a hysteresis zone (HYST) that is used to avoid the jitter (e.g., the unstable toggling between NEAR and FAR states around a threshold, for example, TH1(W1)) of the proximity detection result.

Figure 4C:
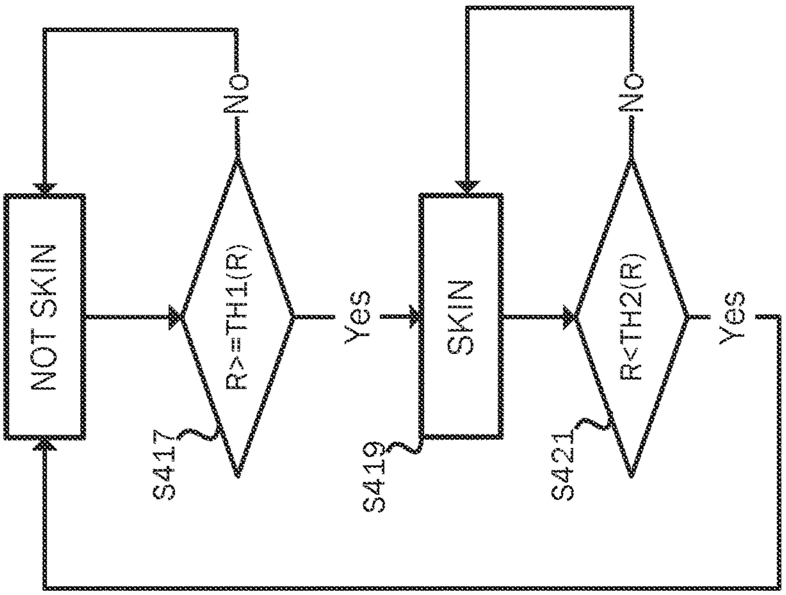
FIG. 4C shows an example of a flow of the wearable device for detecting the presence of skin.

The reflectivity of the first light relative to the skin is different from that of the second light, so the wearable device can detect the presence of the skin according to the intensity comparison between the first light and the second light. FIG. 4C shows an example of a skin detection flow 420 of the wearable device aforementioned for detecting the presence of skin. As shown in S417, when the wearable device starts to perform the skin detection flow 420 from the NOT SKIN state, the wearable device is configured to calculate a ratio R of the intensity of first light S(W1) to the intensity of second light S(W2) and compare the ratio R to a first threshold TH1(R) associated with skin detection. As shown in S419, if the ratio R is not less than the first threshold TH1(R) associated with skin detection, the object is regarded as skin and the wearable device enters into the SKIN state to prepare for performing the subsequent bioinformation measurement. That is to say, the wearable device detects the presence of skin. Otherwise, the object is not regarded as skin and the wearable device returns to NOT SKIN state and recalculates the ratio R. That is to say, the wearable device detects the absence of skin. As shown in S421, when the wearable device detects the presence of skin and is in the SKIN state, the wearable device is continuously configured to calculate a ratio R of the intensity of first light S(W1) to the intensity of second light S(W2) and compare the ratio R to a second threshold TH2(R) associated with skin detection. If the ratio R is less than the second threshold TH2(R) associated with skin detection, the wearable device detects the absence of skin and returns to NOT SKIN state and recalculates the ratio R. Otherwise, the wearable device detects the presence of skin and stays in the SKIN state. The second threshold TH2(R) associated with skin detection is smaller than the first threshold TH1(R) associated with skin detection. The gap between the second threshold TH2(R) associated with skin detection and the first threshold TH1(R) associated with skin detection is a hysteresis zone that is used to avoid the jitter (e.g., the unstable toggling between NEAR and SKIN states around a threshold, for example, TH1(R)) of the skin detection result.

Figure 4D:
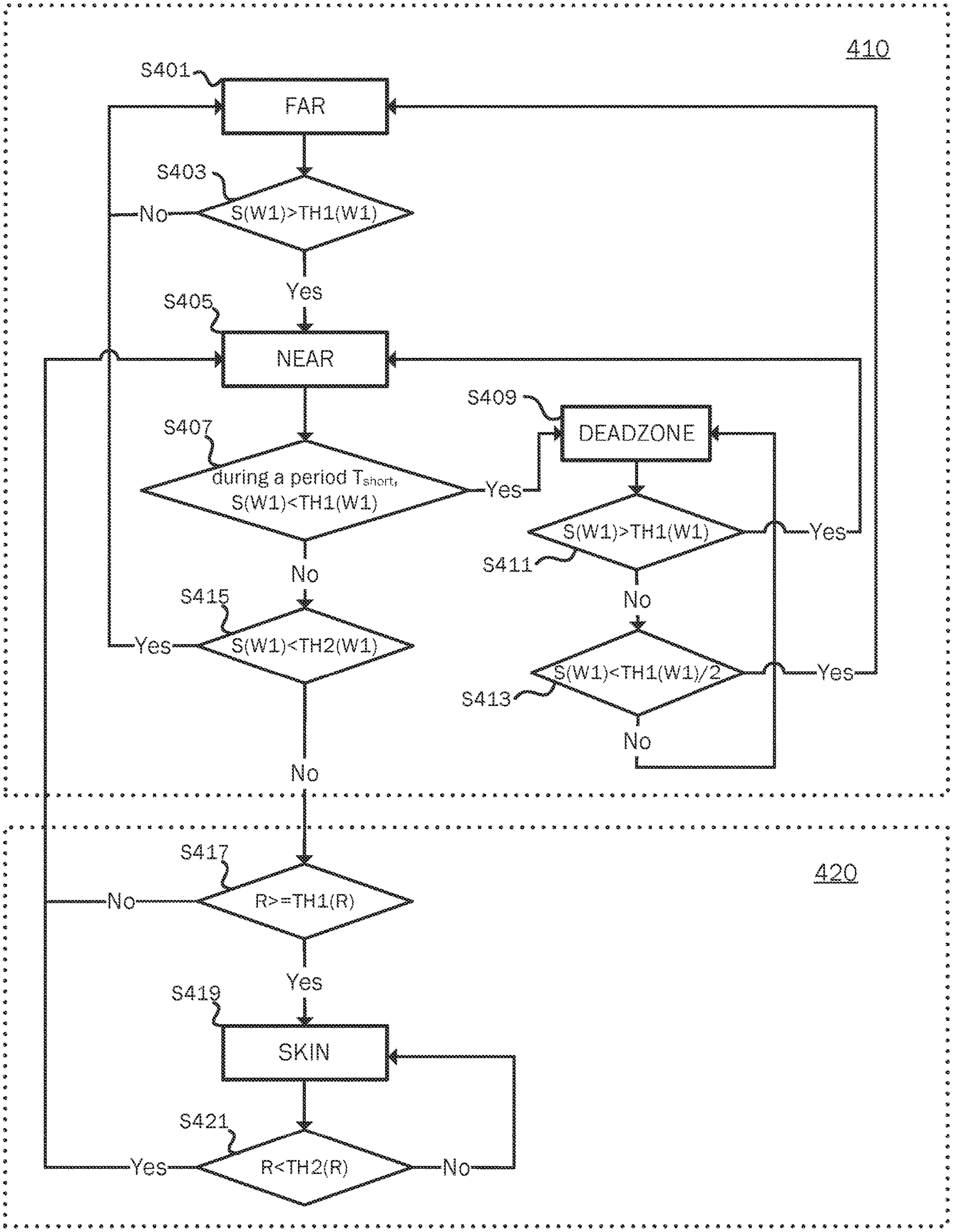
FIG. 4D shows another example of a flow of the wearable device for detecting the presence of skin.

FIG. 4D shows another example of a flow of the wearable device aforementioned for detecting the presence of skin. As shown in FIG. 4D, the wearable device can perform the proximity detection flow 410 first and then perform the skin detection flow 420. In details, when the wearable device detects the object proximity, the wearable device is ready to detect the presence of skin. In the skin detection flow 420, when the wearable device starts to perform the skin detection flow 420, if the intensity of first light S(W1) is less than the first threshold TH1(R) associated with skin detection, the object is not regarded as skin and the wearable device returns to the NEAR state. When the wearable device detects the presence of skin and is in the SKIN state, if the ratio R is less than the second threshold TH2(R) associated with skin detection, the wearable device detects the absence of skin and returns to the NEAR state. The flows of the proximity detection flow 410 and the skin detection flow 420 are the same as the aforementioned flows and can refer to the relevant descriptions.

Figure 4E:
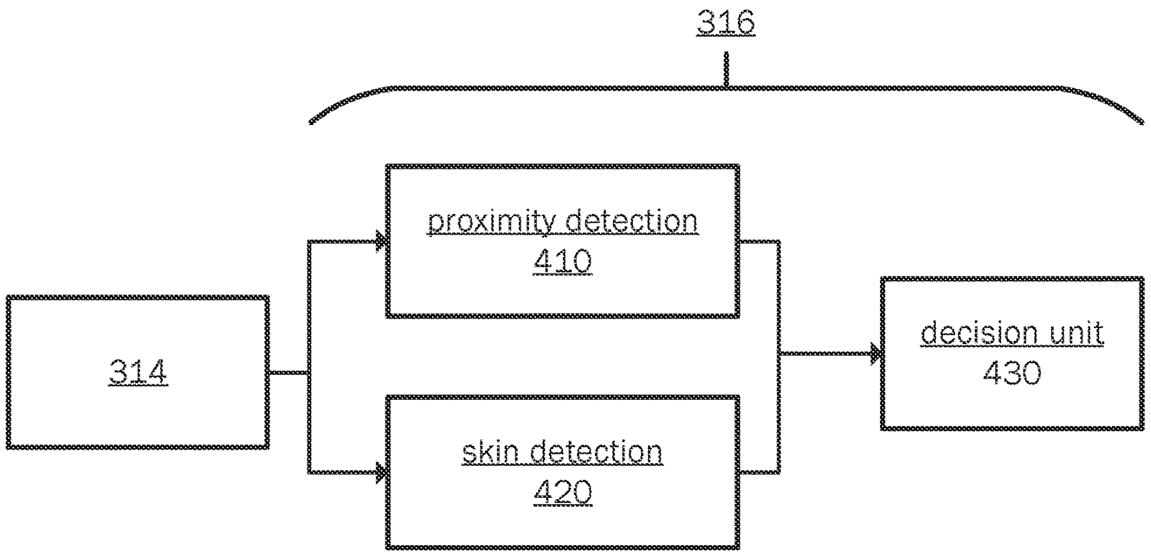
FIG. 4E shows another example of a flow of the wearable device for detecting the presence of skin.

FIG. 4E shows another example of a flow of the wearable device aforementioned for detecting the presence of skin. As shown in FIG. 4E, the proximity detection flow 410 and the skin detection flow 420 can be performed at the same time, and each outputs a detection result to a decision unit 430. If the result of the proximity detection is NEAR and the result of the skin detection is SKIN, the decision unit 430 would output a result indicative of the presence of skin. In an implementation, the proximity detection flow 410, the skin detection flow 420, and the decision unit 430 are implemented by the control circuitry 316.

Figure 4F:
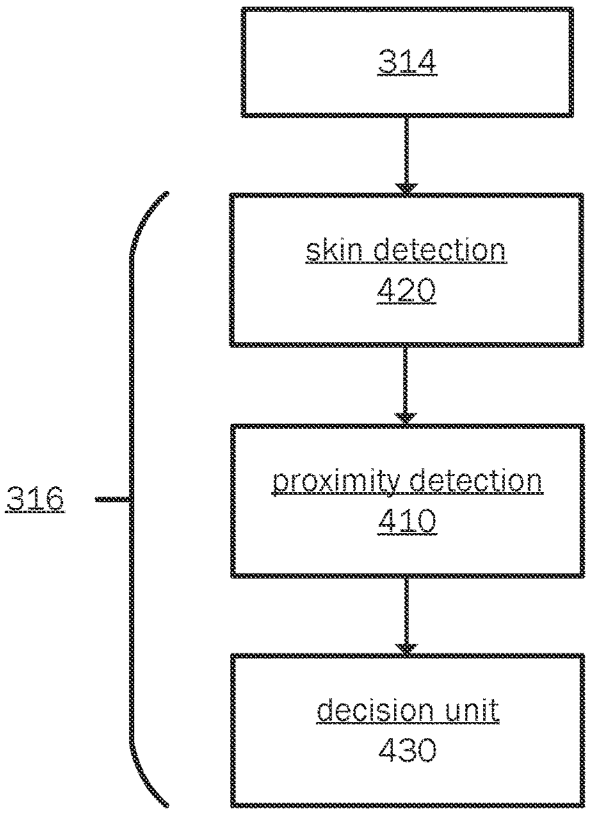
FIG. 4F shows another example of a flow of the wearable device for detecting the presence of skin.

FIG. 4F shows another example of a flow of the wearable device aforementioned for detecting the presence of skin. As shown in FIG. 4F, the wearable device can perform the skin detection flow 420 first and then perform the proximity detection flow 410 and each outputs a detection result to a decision unit 430. If the result of the proximity detection flow 410 is NEAR and the result of the skin detection flow 420 is SKIN, the decision unit 430 would output a result indicative of the presence of skin.

Figure 5:
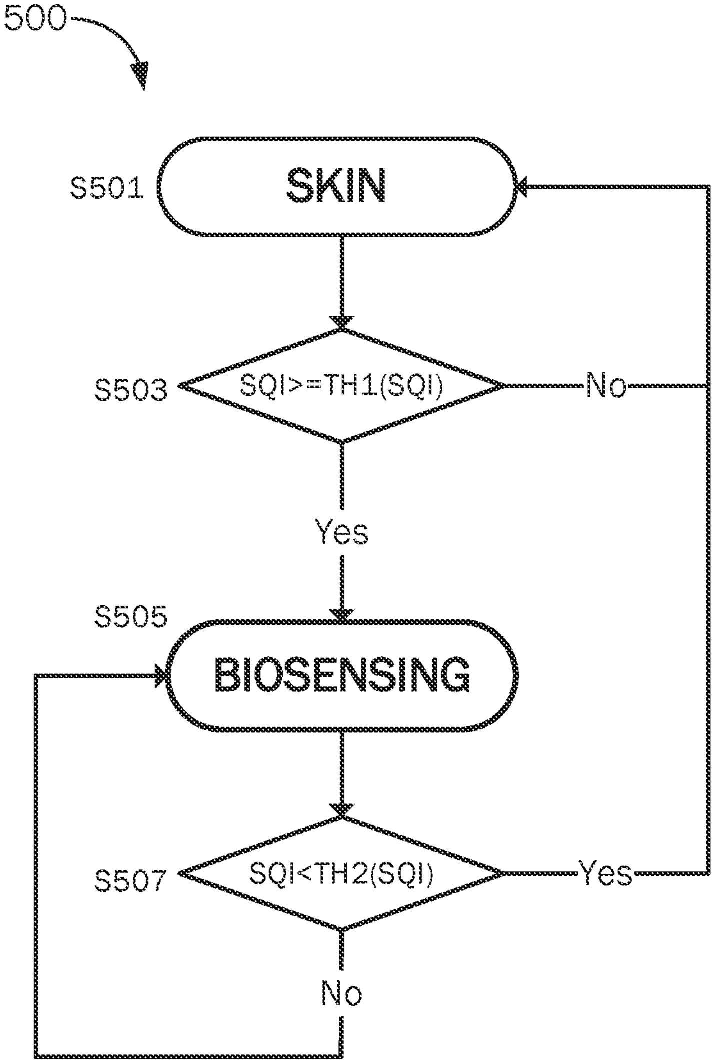
FIG. 5 shows an example of a flow of the wearable device for bioinformation measurement.

FIG. 5 shows a flow 500 of the wearable device aforementioned for bioinformation measurement. As shown in S501, when the wearable device detects the presence of skin and is in the SKIN state, the wearable device is configured to calculate a signal quality SQI associated with a sensor measurement information and compare the SQI to a first threshold TH1(SQI) associated with signal quality, as shown in S503. As shown in S505, if SQI is not less than the first threshold TH1(SQI) associated with signal quality, the wearable device can enter the BIOSENSING state to prepare to perform the bioinformation measurement. Otherwise, the wearable device stays in the SKIN state without performing the bioinformation measurement. As shown in S507, when the wearable device is in the BIOSENSING state, the wearable device is continuously configured to calculate a signal quality SQI associated with a sensor measurement information and compare the SQI to a second threshold TH2(SQI) associated with signal quality. If the SQI is less than the second threshold TH2(SQI) associated with signal quality, the signal quality associated with a sensor measurement information is not good enough to perform the bioinformation measurement and the wearable device stops performing the bioinformation measurement and returns to the SKIN state. Otherwise, the wearable device stays in the BIOSENSING state. The second threshold TH2(SQI) associated with signal quality is smaller than the first threshold TH1(SQI) associated with signal quality. The gap between the second threshold TH2(SQI) associated with signal quality and the first threshold TH1(SQI) associated with signal quality is a hysteresis zone (HYST) that is used to avoid the jitter (e.g., the unstable toggling between SKIN and BIOSENSING states around a threshold, for example, TH1(SQI)) of the bioinformation measurement result.

Referring back to FIG. 1, in some implementations, once the first wearable device 110 and the second wearable device 120 each determines one or more first characteristics associated with the first sensor measurement information and one or more second characteristics associated with the second sensor measurement information, the first wearable device 110 and the second wearable device 120 can transmit data representing the characteristics associated with the sensor measurement information (e.g., signal quality) to each other. Each wearable device 110/120 may then determine independently, based on a comparison between the one or more first and second characteristics, which wearable device is to continue performing the bioinformation measurement, and which wearable device is to send the sensor measurement information to the computing device 130 (e.g., smart phone) for further processing.

As an example, if the user has not properly placed the second wearable device 120 in his ear, the bioinformation measured by the second wearable device 120 may have a lower signal quality due to weaker received light or higher noises from the ambient environment. The first wearable device 110 and the second wearable device 120 may each determine that the first wearable device 110 is to transmit the first sensor measurement information to the computing device 130 based on a comparison between a signal quality associated with the first sensor measurement information and a signal quality associated with the second sensor measurement information.

In some implementations, in response to determining that the first wearable device 110 is to send the sensor measurement information to the computing device 130, the second wearable device 120 may control the second sensor to enter into a power-saving mode. For example, in response to determining that the first wearable device 110 is to send the sensor measurement information to the computing device 130, the second wearable device 120 may control the second sensor to enter into the power-saving mode by controlling the second sensor to stop obtaining the second sensor measurement information. As another example, the second wearable device 120 may control the second sensor to enter into the power-saving mode by controlling the second sensor to stop transmitting the second sensor measurement information. In some other implementations, the first wearable device 110 may transmit control data to the second wearable device 120 to cause the second sensor to stop obtaining the second sensor measurement information and/or transmitting the second sensor measurement information to the first wearable device 110 and the computing device 130.

In some implementations, after entering the power-saving mode, the second wearable device 120 may control the second sensor to exit the power-saving mode if a threshold has been met (e.g., a timer for the power-saving mode has reached a threshold time) or if an event has been triggered (e.g., the user took out the earbud from his/her ear and then put it back in again).

Figure 2:
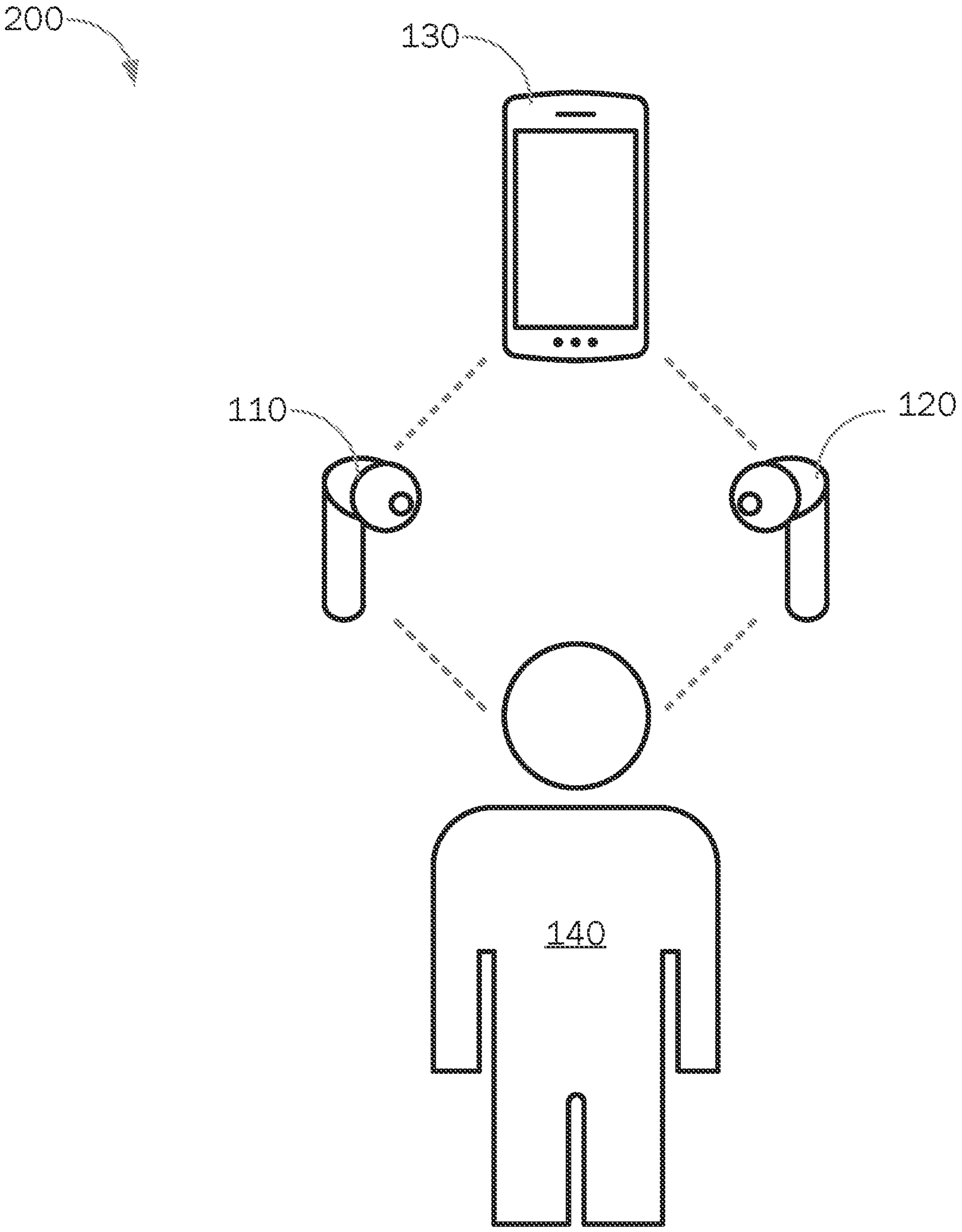
FIG. 2 shows an example of an optical sensing system.

FIG. 2 shows another example of an optical sensing system 200. In the optical sensing system 200, the first wearable device 110 and the second wearable device 120 each transmits to the computing device 130 the respective sensor measurement information and/or the respective one or more characteristics associated with the sensor measurement information. The computing device 130 is configured to determine, based on a comparison between the one or more first and second characteristics, which wearable device is to continue performing the bioinformation measurement, and which wearable device is to send the sensor measurement information to the computing device 130 for further processing. For example, in response to determining that the first wearable device 110 should continue performing the bioinformation measurement and transmitting the sensor measurement information to the computing device 130, the computing device 130 may send a signal to the second wearable device 120 to enter a power-saving mode (e.g., stop obtaining bioinformation measurements and/or stop transmitting sensor measurement information).

Figure 6:
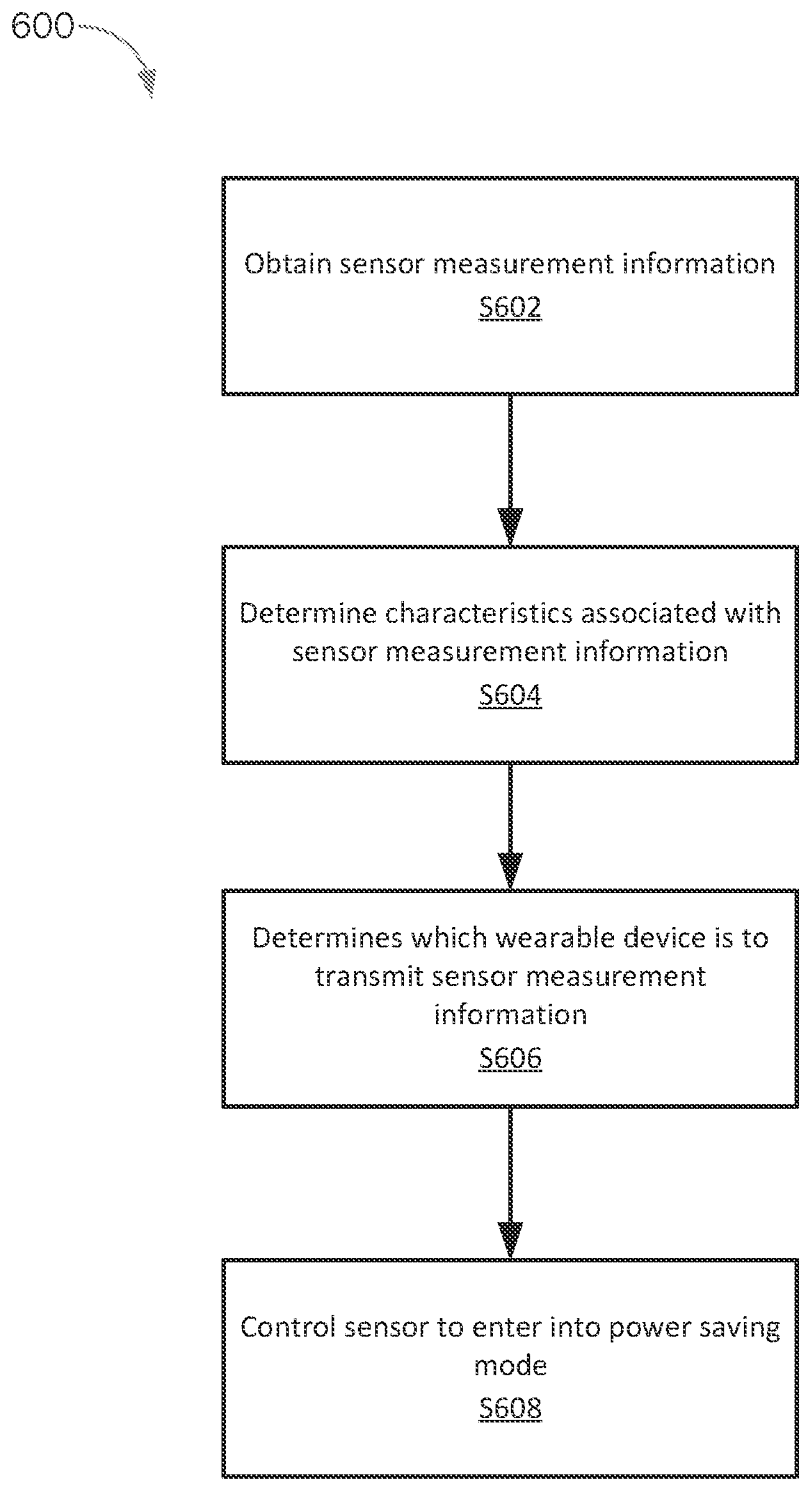
FIG. 6 shows an example of a flow for controlling sensor measurement information transmission.

FIG. 6 shows an example flow chart 600 for controlling transmission of sensor measurement information. The flow chart 600 may be implemented by a system such as the optical sensing system 100 or the optical sensing system 200.

The system obtains first sensor measurement information representing a particular type of bioinformation measured from a first part of a user and second sensor measurement information representing the particular type of bioinformation measured from a second part of the user (S602). For example, the first wearable device 110 (e.g., a first earbud) and the second wearable device 120 (a second earbud) may use SWIR light to collect a user's heartrate information from portions of the user's skin (e.g., ears) in contact with the wireless earbuds.

The system determines one or more first characteristics associated with the first sensor measurement information and one or more second characteristics associated with the second sensor measurement information (S604). For example, each of the first wearable device 110 and the second wearable device 120 may determine its respective signal quality for bioinformation measurements and/or battery power level.

The system determines which wearable device is to transmit sensor measurement information to a computing device based on a comparison between the one or more first characteristics and the one or more second characteristics (S606). For example, the first wearable device 110 and the second wearable device 120 may each determine that the first wearable device 110 is to transmit the first sensor measurement information to the computing device 130 based on a comparison between a signal quality associated with the first sensor measurement information and a signal quality associated with the second sensor measurement information. As another example, the computing device 130 may determine, based on a comparison between the one or more first and second characteristics, which wearable device is to continue performing the bioinformation measurement, and which wearable device is to send the sensor measurement information to the computing device 130 for further processing.

The system controls a sensor to enter into a power-saving mode (S608). In some implementation, the system controls a sensor to enter into a power-saving mode by controlling, by one or more of the first wearable device 110, the second wearable device 120, or the computing device 130, the second sensor to stop obtaining the second sensor measurement information. For example, in response to determining that the first wearable device 110 is to send the sensor measurement information to the computing device 130, the second wearable device 120 may control the second sensor to enter into the power-saving mode by controlling the second sensor to stop obtaining the second sensor measurement information.

Figure 7:
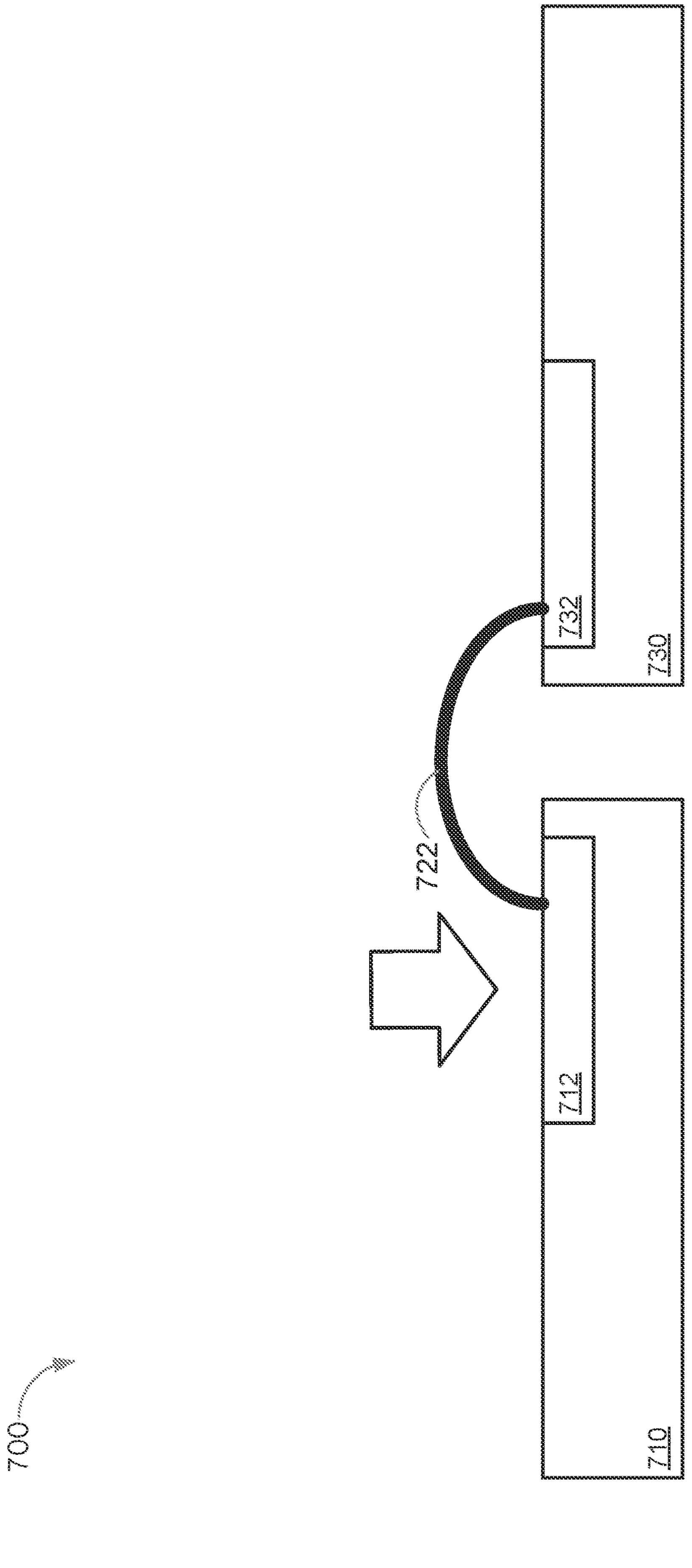
FIG. 7 shows an example of an optical sensor.

FIG. 7 illustrates an example of a photodetector 700. The photodetector 700 includes a first substrate 710 and a second substrate 730. The first substrate 710 includes a sensing area 712 (e.g., III-V material) that is electrically coupled to sensing circuitry 732 (e.g., CMOS circuitry) of the second substrate 730 via wire(s) 722 (e.g., wire-bonded).

Figure 8:
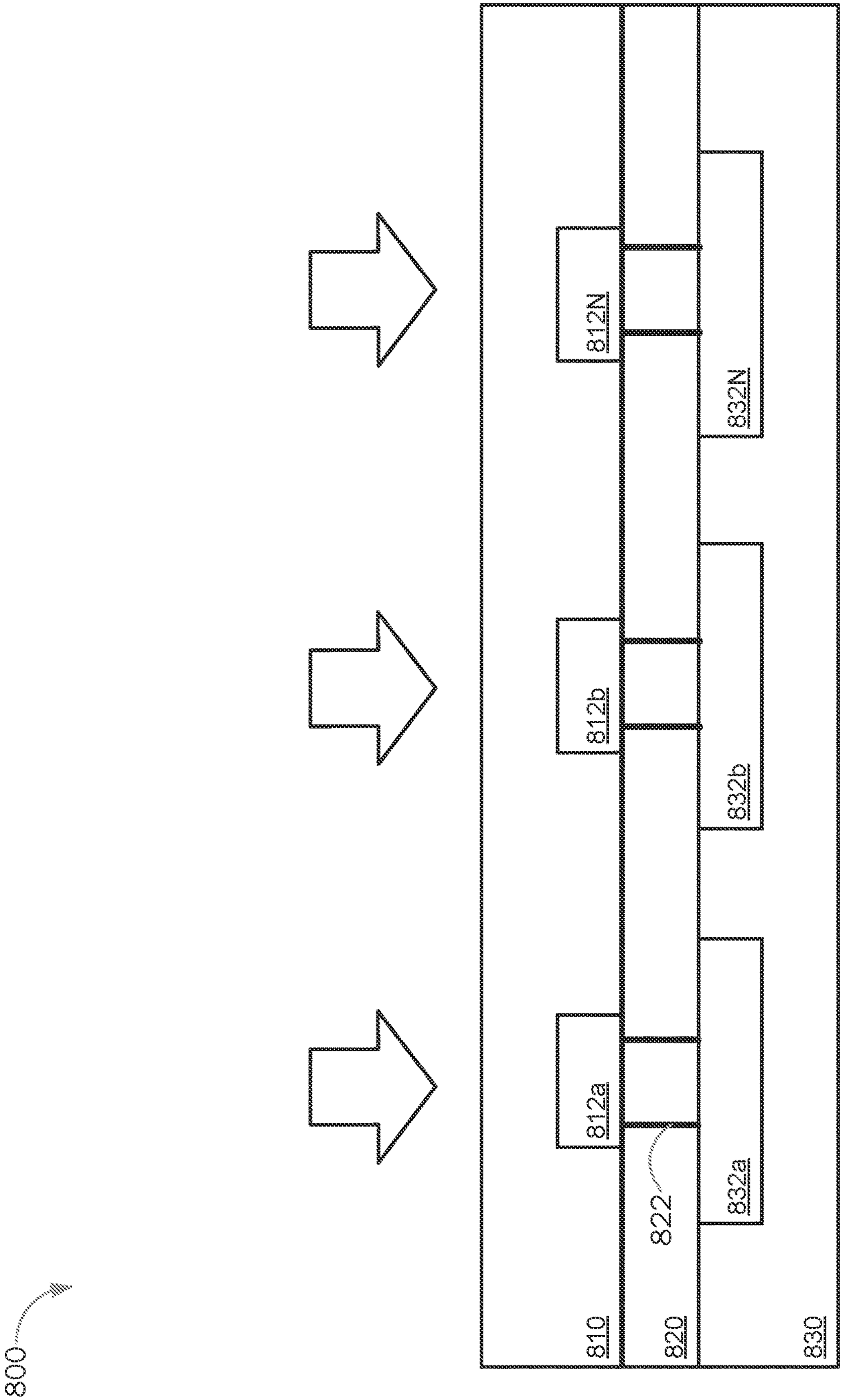
FIG. 8 shows an example of an optical sensor.

FIG. 8 illustrates an example of a photodetector 800. The photodetector 800 includes a first substrate 810 and a second substrate 830, which can both be silicon substrate. The first substrate 810 and the second substrate 830 are wafer-bonded via a bonding interface 820 (e.g., oxide or any other suitable materials). The first substrate 810 includes multiple sensing areas 812*a*~812N, where Nis a positive integer. In some implementations, the multiple sensing areas 812*a*~812N may be comprised of germanium that is deposited on the silicon substrate 810. The second substrate 830 includes multiple corresponding circuitry areas 832*a*~832N. The multiple sensing areas 812*a*~812N and the multiple corresponding circuitry areas 832*a*~832N are electrically coupled through the bonding interface 820 via wires 822.

In some cases, the sensor configured to detect optical signals may be exposed to an environment with excessive or insufficient light intensity. The sensing signals detected by the sensor may be affected by ambient light, resulting in a deterioration of the signal-to-noise ratio (SNR) or saturating the sensor to fail to sense the signal. In that case, the determination of the detection result or the bioinformation measurement based on the sensing signals may cause inaccuracy. Referring back to FIG. 3, the receiver module 314 of sensor 310 may further include at least one amplifier (e.g., transimpedance amplifier, TIA) and an analog-to-digital converter (ADC) to amplify and convert the received light into digital signals for transmission to the control circuitry 316 for detection result determination or bioinformation measurement process. In some implementations, the ambient light intensity is too strong or insufficient, and the sensor 310 may include a gain adjustment mechanism to dynamically adjust the amplification gain of the receiver module 314 to maintain the SNR of the sensing signals within an acceptable range for the subsequent process.

Figure 9:
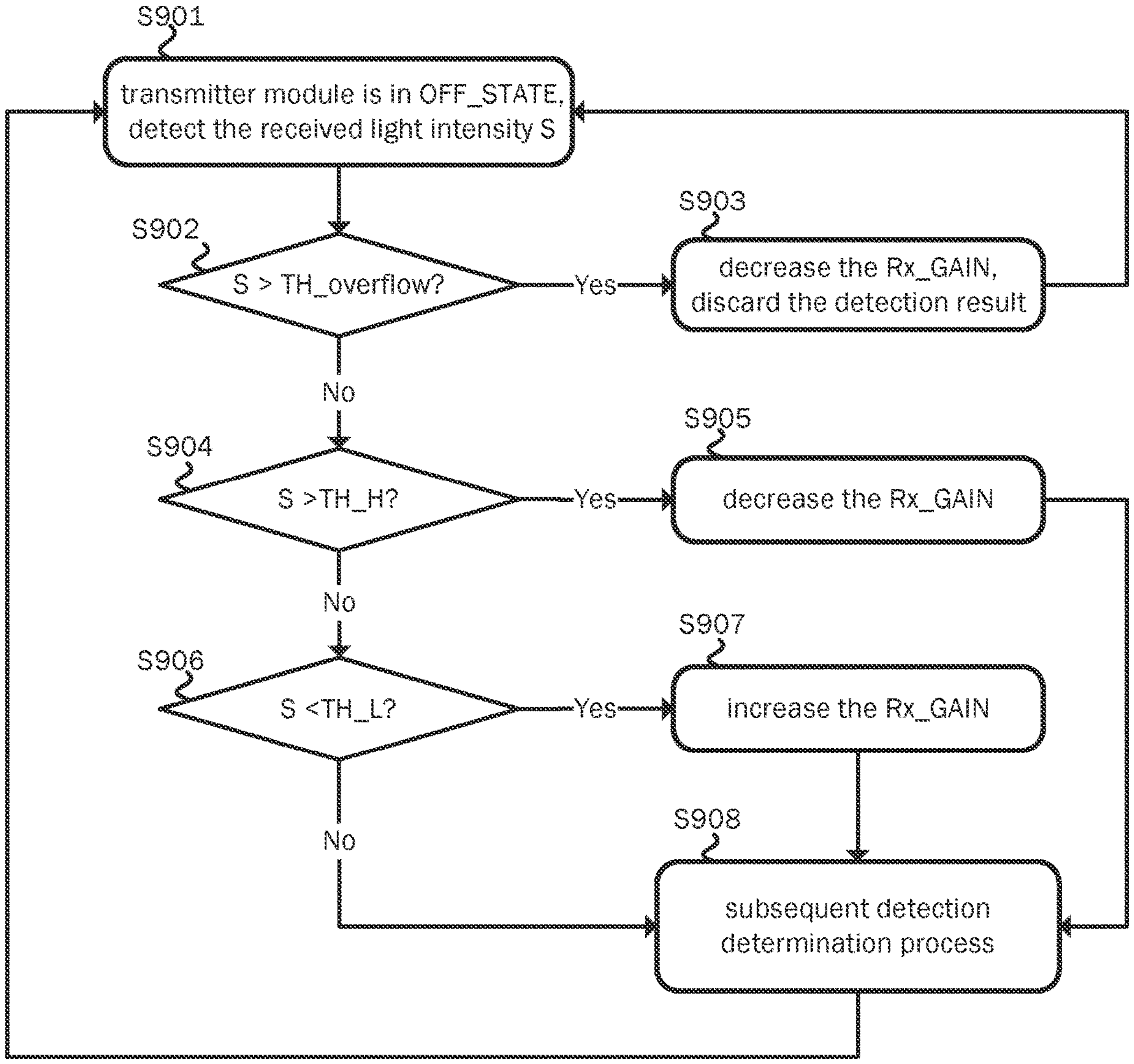
FIG. 9 shows an example of a flow of gain adjustment mechanism for the sensor.

FIG. 9 shows an example of a flow of gain adjustment mechanism for the sensor. The ADC output of the sensor may include a first threshold (TH_overflow), a second threshold (TH_H), and a third threshold (TH_L) associated with the gain adjustment process for the received light intensity to judge the gain adjustment of the receiver module. The first threshold (TH_overflow) is close to the upper limit of the light intensity that the receiver module can receive. The first threshold (TH_overflow) is greater than the second threshold (TH_H), and the second threshold (TH_H) is greater than the third threshold (TH_L). When the intensity of received light is greater than the first threshold (TH_overflow), the sensing signals may be seriously deteriorated due being too close to the saturation operating region of the receiver module. When the intensity of received light is between the first threshold (TH_overflow)

and the second threshold (TH_H), the SNR of the sensing signals needs to be enhanced because the amplification gain of the receiver module is too large. When the intensity of received light is lower than the third threshold (TH_L), the SNR of the sensing signals needs to be enhanced because the amplification gain of the receiver module is too small. The flow of gain adjustment mechanism may be implemented in circuitry of the sensor or in firmware for driving the sensor.

As shown in S901, when the transmitter module of the sensor is not activated (OFF_STATE) and the receiver module of the sensor is still activated, the gain adjustment process is performed. At this time, the received light intensity S is detected to inspect whether the gain of the receiver module needs to be adjusted. In some implementations, the received light intensity S can be obtained from an output of the ADC. Then, as shown in S902, the received light intensity S is compared to the first threshold (TH_overflow). As shown in S903, while the received light intensity S is greater than the first threshold (TH_overflow), the sensor decreases (e.g., reduce the gain by half, a quarter, or a predetermined factor) the amplification gain (Rx_GAIN) of the receiver module. In some implementations, the sensor discards the detection result of the receiver module due to severe degradation of the sensing signal. Then, as shown in S901, the gain adjustment process is restarted again. As shown in S904, while the received light intensity S is not greater than the first threshold (TH_overflow), the received light intensity S is compared to the second threshold (TH_H). As shown in S905, while the received light intensity S is less than the first threshold (TH_overflow) and greater than the second threshold (TH_H), the sensor decreases (e.g., reduce the gain by half, a quarter, or a predetermined factor) the amplification gain (Rx_GAIN) of the receiver module to enhance the SNR of the sensing signals and the subsequent detection determination process is performed, as shown in S908. Then, as shown in S901, the dynamic adjustment of the amplification gain (Rx_GAIN) is continued by repeatedly performing the gain adjustment process.

As shown in S906, while the received light intensity S is not greater than the second threshold (TH_H), the received light intensity S is compared to the third threshold (TH_L). As shown in S907, while the received light intensity S is less than the third threshold (TH_L), the sensor increases (e.g., increase the gain by 2, 4, or a predetermined factor) the amplification gain (Rx_GAIN) of the receiver module to enhance the SNR of the sensing signals and the subsequent detection determination process is performed, as shown in S908. Then, as shown in S901, the dynamic adjustment of the amplification gain (Rx_GAIN) is continued by repeatedly performing the gain adjustment process. While the received light intensity S is less than the second threshold (TH_H) and greater than the third threshold (TH_L), the amplification gain (Rx_GAIN) of the receiver module would not be adjusted and the subsequent detection determination process is performed, as shown in S908. Then, as shown in S901, the dynamic adjustment of the amplification gain (Rx_GAIN) is continued by repeatedly performing the gain adjustment process. The subsequent detection determination process can include but is not limited to proximity detection, skin detection, or bioinformation measurement.

In some cases, when a device with a sensor may be not placed in the proper location or may stop operation for a while, the device may enter a power-saving mode (e.g., system-on-chip may be configured to enter a power-saving mode) to reduce the power consumption of the device. The device may include a motion sensor configured to detect the movement of the device and/or a proximity sensor configured to detect the proximity to the object. In some cases, when the device is operated in power-saving mode, the device can be woken up by the detection result of the motion sensor or the proximity sensor. For example, when the device is moved or changed location, the motion sensor can send a detection result in response to the movement, and the device can be woken up based on the detection result from the motion sensor. For another example, when the device is moved to proximity to an object, the proximity sensor can send a detection result in response to the proximity detection, and the device can be woken up based on the detection result from the proximity sensor. However, if the device is used for a human, such as a wearable device, the detection result from the motion sensor and/or the proximity sensor may provide a false detection result of the presence of the human. For example, if the device placed on the table only changes its position on the table, or if the device is close to a non-living body, the motion sensor and the proximity sensor may send detection results to falsely wake up the device. Therefore, the device wastes unnecessary power consumption.

Figure 10:
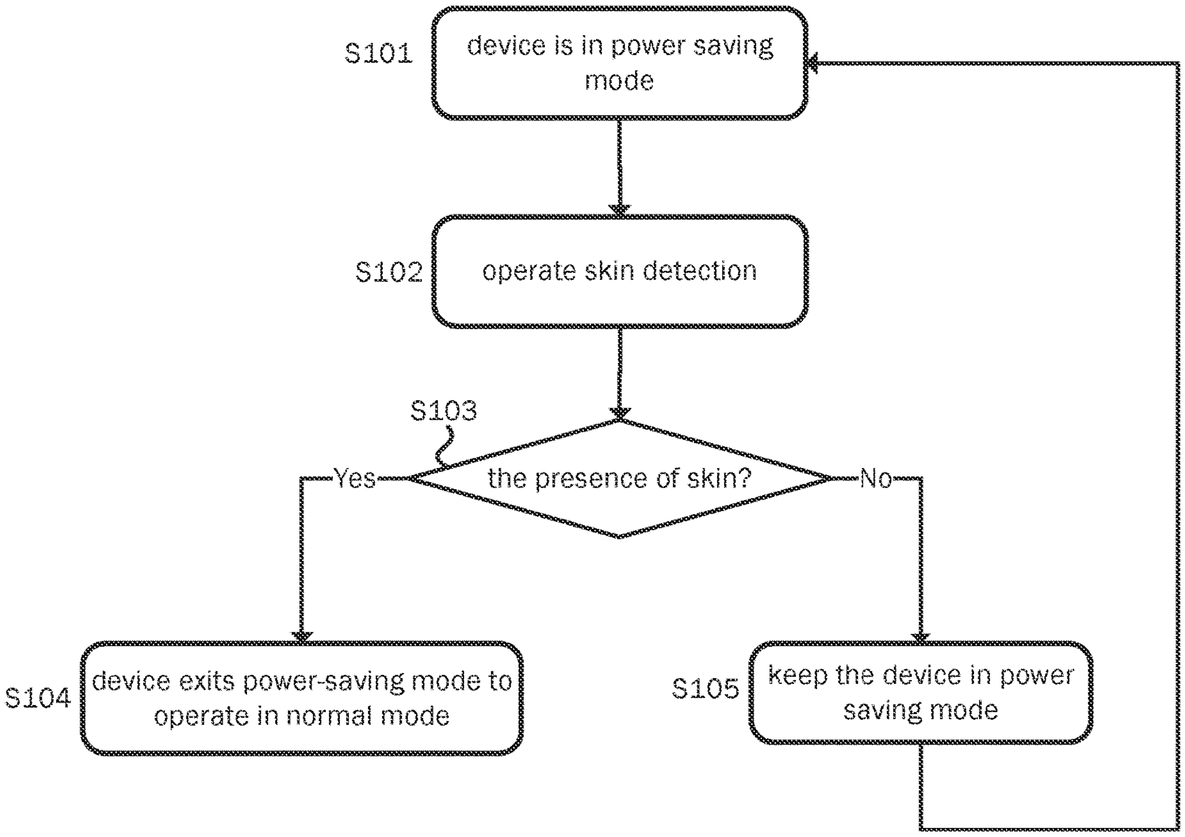
FIG. 10 shows an example of a flow of the wake-up process for a device.

FIG. 10 shows an example of a flow of the wake-up process for a device. Referring back to FIG. 3, when the device enters the power-saving mode, the device 300 may allow a system-on-chip (SOC) which may include the input module 320, the output module 330, the communication module 340, and/or other circuitry 350 to operate at low power or even disable for power saving. However, the skin detection circuitry in the sensor 310 is allowed to operate a skin detection function periodically to determine to return to normal mode operation. When the device operates in a power-saving mode (as shown in S101), the skin detection circuitry is allowed to operate the skin detection function periodically (as shown in S102) to detect the presence of skin (as shown in S103). As shown in S104, when the detection result of skin detection indicates the skin is present, the skin detection circuitry outputs a signal that cause the device to exit the power-saving mode and to operate in the normal mode. As shown in S105, when the detection result of skin detection indicates the skin isn't present, the device is not woken up so that it still operates in the power-saving mode. The wake-up determination is determined by the detection result of the skin detection, which can reduce false wake-up and reduce power consumption.

While the disclosure has been described by way of example and in terms of a preferred embodiment, it is to be understood that the disclosure is not limited thereto. On the contrary, it is intended to cover various modifications and similar arrangements and procedures, and the scope of the appended claims therefore should be accorded the broadest interpretation so as to encompass all such modifications and similar arrangements and procedures.

What is claimed is:

1. A method for operating a wearable device to detect a presence of skin, comprising:

- detecting, by a receiver module of the wearable device, a first light with a first wavelength, wherein the receiver module comprises one or more photodetectors;
- determining, by circuitry of the wearable device, that the wearable device has entered and remained in a near state by:
  - determining that an intensity of the first light exceeds a first proximity threshold;
  - in response to determining that the intensity of the first light exceeds the first proximity threshold, entering into the near state;

detecting, by the receiver module, a second light with the first wavelength; and determining, by the circuitry, that the wearable device is not in a deadzone state and remains in the near state by determining that an intensity of the second light does not decrease below the first proximity threshold for a predetermined period of time during which the wearable device is in the near state, the wearable device entering the deadzone state in response to determining that the intensity of the second light decreased below the first proximity threshold within the predetermined period of time, the deadzone state representing the receiver module being closer to the skin than in the near state;

in response to determining that the wearable device is not in the deadzone state and remains in the near state, detecting, by the receiver module, a third light with the first wavelength and a fourth light with a second wavelength;

determining, by the circuitry, the presence of the skin based on a comparison between (i) a first ratio between an intensity of the third light and an intensity of the fourth light and (ii) a first skin-detection threshold;

in response to determining the presence of the skin, entering a skin state and performing, by the wearable device, a bioinformation measurement;

detecting, by the receiver module, a fifth light with the first wavelength and a sixth light with the second wavelength;

determining, by the circuitry, an absence of the skin based on a comparison between (i) a second ratio between an intensity of the fifth light and an intensity of the sixth light and (ii) a second skin-detection threshold that is different from the first skin-detection threshold;

in response to determining the absence of the skin, leaving the skin state and entering the near state;

detecting, by the receiver module, a seventh light with the first wavelength;

determining, by the circuitry, that an intensity of the seventh light is less than a second proximity threshold that is less than the first proximity threshold; and in response to determining that the intensity of the seventh light is less than the second proximity threshold, entering into a far state.

2. The method of claim 1, wherein the first skin-detection threshold is higher than the second skin-detection threshold.

3. The method of claim 1, further comprising calculating, by the circuitry of the wearable device, a signal quality associated with a sensor measurement information, and determining to perform the bioinformation measurement based on a comparison between the signal quality associated with the sensor measurement information and a first signal-quality threshold.

4. The method of claim 3, further comprising determining to stop the bioinformation measurement based on a comparison between the signal quality associated with the sensor measurement information and a second signal-quality threshold.

5. The method of claim 3, wherein the signal quality associated with the sensor measurement information comprises a weighted calculation of one or more of an AC signal amplitude of a particular sensor measurement, a signal-to-noise ratio of the particular sensor measurement, or a DC drift variation of the particular sensor measurement.

6. The method of claim 3, wherein the bioinformation measurement comprises a heart rate, a skin moisture, or a blood pressure of a user.

7. The method of claim 3, wherein calculating, by the circuitry of the wearable device, the signal quality further comprises calculating the signal quality after determining that the skin is present.

8. The method of claim 1, wherein the first wavelength is within a near-infrared (IR) wavelength range and the second wavelength is within a short-wave infrared (SWIR) wavelength range.

9. The method of claim 1, wherein the first wavelength and the second wavelength are within a SWIR wavelength range.

10. The method of claim 1, wherein determining the presence of the skin is in response to the first ratio being greater than the first skin-detection threshold.

11. The method of claim 1, wherein determining the absence of the skin is in response to the second ratio being less than the second skin-detection threshold.

12. The method of claim 1, further comprising in response to determining the absence of the skin, providing, by the circuitry of the wearable device, a control signal to enter into a power-saving mode.

13. A wearable device comprising:

a sensor comprising a receiver module and circuitry;

wherein the sensor is configured to:

detect, by the receiver module, a first light with a first wavelength, wherein the receiver module comprises one or more photodetectors;

determine, by the circuitry, that the wearable device has entered and remained in a near state by determining that an intensity of the first light exceeds a first proximity threshold;

in response to determining that the intensity of the first light exceeds the first proximity threshold, enter into the near state;

detect, by the receiver module, a second light with the first wavelength; and determine, by the circuitry, that the wearable device is not in a deadzone state and remains in the near state by determining that an intensity of the second light does not decrease below the first proximity threshold for a predetermined period of time during which the wearable device is in the near state, the wearable device entering the deadzone state in response to determining that the intensity of the second light decreased below the first proximity threshold within the predetermined period of time, the deadzone state representing the receiver module being closer to the skin than in the near state;

in response to determining that the wearable device is not in the deadzone state and remains in the near state, detect, by the receiver module, a third light with the first wavelength and a fourth light with a second wavelength;

determine, by the circuitry, a presence of skin based on a comparison between (i) a first ratio between an intensity of the third light and an intensity of the fourth light and (ii) a first skin-detection threshold;

in response to determining the presence of the skin, enter a skin state and perform a bioinformation measurement;

detect, by the receiver module, a fifth light with the first wavelength and a sixth light with the second wavelength;

determine, by the circuitry, an absence of the skin based on a comparison between (i) a second ratio between an intensity of the fifth light and an intensity of the sixth light and (ii) a second skin-detection threshold that is different from the first skin-detection threshold;

in response to determining the absence of the skin, leave the skin state and enter the near state;

detect, by the receiver module, a seventh light with the first wavelength;

determine, by the circuitry, that an intensity of the seventh light is less than a second proximity threshold that is less than the first proximity threshold; and in response to determining that the intensity of the seventh light is less than the second proximity threshold, enter into a far state.

* * * * *